US011511056B2

(12) United States Patent
Hepworth et al.

(10) Patent No.: US 11,511,056 B2
(45) Date of Patent: Nov. 29, 2022

(54) APPARATUS FOR GENERATING AN INHALABLE MEDIUM

(71) Applicant: British American Tobacco (Investments) Limited, London (GB)

(72) Inventors: Richard Hepworth, London (GB); Joseph Sutton, London (GB); Dominic Woodcock, London (GB); Sharon Goodall, London (GB)

(73) Assignee: Nicoventures Trading Limited, London (GB)

(*) Notice: Subject to any disclaimer, the term of this patent is extended or adjusted under 35 U.S.C. 154(b) by 272 days.

(21) Appl. No.: 15/764,581

(22) PCT Filed: Sep. 30, 2016

(86) PCT No.: PCT/EP2016/073472
§ 371 (c)(1),
(2) Date: Mar. 29, 2018

(87) PCT Pub. No.: WO2017/055584
PCT Pub. Date: Apr. 6, 2017

(65) Prior Publication Data
US 2018/0279678 A1      Oct. 4, 2018

(30) Foreign Application Priority Data

Oct. 2, 2015 (GB) .................................... 1517471

(51) Int. Cl.
*A61M 15/06* (2006.01)
*A61M 11/04* (2006.01)
(Continued)

(52) U.S. Cl.
CPC ............. *A61M 15/06* (2013.01); *A24D 1/002* (2013.01); *A24F 40/30* (2020.01); *A24F 40/42* (2020.01);
(Continued)

(58) Field of Classification Search
CPC ........ A24F 47/008; A24F 40/10; A24F 40/30; A61M 11/042
See application file for complete search history.

(56) References Cited

U.S. PATENT DOCUMENTS 4,083,372 A   4/1978 Boden
4,756,318 A   7/1988 Clearman et al.
(Continued)

FOREIGN PATENT DOCUMENTS

AT      507187 A4    3/2010
AT      507187 B1    3/2010
(Continued)

OTHER PUBLICATIONS

International Search Report, Application No. PCT/EP2016/073472, dated Jan. 31, 2017, 3 pages.
(Continued)

*Primary Examiner* — Erin E McGrath
(74) *Attorney, Agent, or Firm* — Patterson Thuente, P.A.

(57) ABSTRACT

Apparatus and methods for generating an inhalable medium are disclosed. An apparatus includes a container for holding a liquid, a heater for volatilizing liquid held in the container to generate a flow of at least one of a vapor and an aerosol in use, and a receptacle for receiving material. The receptacle is located adjacent to the heater such that in use, material received in the receptacle is heated by the heater. One or more constituents of material received in the receptacle in use are mixed with the flow of at least one of a vapor and an aerosol in use to produce the inhalable medium.

14 Claims, 5 Drawing Sheets

(51) Int. Cl.
  *A24F 40/30* (2020.01)
  *A24F 40/10* (2020.01)
  *A24F 40/20* (2020.01)
  *A24F 40/42* (2020.01)
  *A24F 40/485* (2020.01)
  *A24D 1/00* (2020.01)
  *A61M 15/00* (2006.01)
  *A61M 16/00* (2006.01)

(52) U.S. Cl.
  CPC ......... *A24F 40/485* (2020.01); *A61M 11/042* (2014.02); *A24F 40/10* (2020.01); *A24F 40/20* (2020.01); *A61M 15/0015* (2014.02); *A61M 15/0021* (2014.02); *A61M 2016/0015* (2013.01); *A61M 2205/3653* (2013.01); *A61M 2205/8206* (2013.01)

(56) References Cited

U.S. PATENT DOCUMENTS

| | | |
|---|---|---|
| 4,913,169 A | 4/1990 | Templeton |
| 5,027,836 A | 7/1991 | Shannon et al. |
| 5,027,839 A | 7/1991 | Appell |
| 5,115,820 A | 5/1992 | Hauser et al. |
| 5,203,355 A | 4/1993 | Clearman et al. |
| 5,327,915 A | 7/1994 | Porenski et al. |
| 5,613,505 A | 3/1997 | Campbell et al. |
| 5,820,967 A | 10/1998 | Gadkaree |
| 5,950,619 A | 9/1999 | Van Der Linden |
| 6,095,558 A | 8/2000 | Bayer et al. |
| 6,814,786 B1 | 11/2004 | Zhuang et al. |
| 6,988,496 B1 | 1/2006 | Eicher et al. |
| 7,160,366 B2 | 1/2007 | Blackburn et al. |
| 7,699,052 B2 | 4/2010 | Schiewe et al. |
| 8,833,364 B2 | 9/2014 | Buchberger |
| 8,997,753 B2 | 4/2015 | Li et al. |
| 9,259,031 B2 | 2/2016 | Branton et al. |
| D761,998 S | 7/2016 | Pinder |
| D768,915 S | 10/2016 | Wright et al. |
| 9,456,632 B2 | 10/2016 | Hon |
| D782,728 S | 3/2017 | Pinder |
| D782,729 S | 3/2017 | Wright et al. |
| D805,684 S | 12/2017 | Thuery |
| 9,894,930 B2 | 2/2018 | Bonici et al. |
| D815,342 S | 4/2018 | Sutton |
| D818,635 S | 5/2018 | Pinder et al. |
| D818,638 S | 5/2018 | Wright et al. |
| D825,099 S | 8/2018 | Wright et al. |
| D825,103 S | 8/2018 | Wright et al. |
| 10,375,996 B2 | 8/2019 | Aoun et al. |
| 10,426,199 B2 | 10/2019 | Turner et al. |
| 2004/0194792 A1 | 10/2004 | Zhuang et al. |
| 2005/0133051 A1 | 6/2005 | Luan et al. |
| 2005/0133054 A1 | 6/2005 | Fournier et al. |
| 2006/0144412 A1 | 7/2006 | Mishra et al. |
| 2006/0201524 A1 | 9/2006 | Zhang et al. |
| 2007/0023056 A1 | 2/2007 | Cantrell et al. |
| 2007/0215168 A1 | 9/2007 | Banerjee et al. |
| 2008/0092912 A1 | 4/2008 | Robinson et al. |
| 2008/0110470 A1 | 5/2008 | Zhuang et al. |
| 2008/0241255 A1 | 10/2008 | Rose |
| 2010/0024834 A1 | 2/2010 | Oglesby et al. |
| 2011/0088707 A1 | 4/2011 | Hajaligol |
| 2011/0226236 A1 | 9/2011 | Buchberger |
| 2012/0006346 A1 | 1/2012 | Inagaki |
| 2012/0042885 A1 | 2/2012 | Stone et al. |
| 2012/0199663 A1 | 8/2012 | Qiu |
| 2012/0255567 A1 | 10/2012 | Rose et al. |
| 2012/0318882 A1 | 12/2012 | Abehasera |
| 2013/0014772 A1 | 1/2013 | Liu |
| 2013/0056013 A1 | 3/2013 | Terry et al. |
| 2013/0133675 A1 | 5/2013 | Shinozaki et al. |
| 2013/0160780 A1 | 6/2013 | Matsumoto et al. |
| 2013/0192616 A1 | 8/2013 | Tucker et al. |
| 2013/0192620 A1 | 8/2013 | Tucker et al. |
| 2013/0298905 A1 | 11/2013 | Levin et al. |
| 2013/0333700 A1 | 12/2013 | Buchberger |
| 2014/0048085 A1 | 2/2014 | Cox |
| 2014/0076340 A1 | 3/2014 | Kizer et al. |
| 2014/0123989 A1 | 5/2014 | Lamothe |
| 2014/0159250 A1 | 6/2014 | Nickerson |
| 2014/0166029 A1 | 6/2014 | Weigensberg et al. |
| 2014/0190502 A1 | 7/2014 | Liu |
| 2014/0261486 A1 | 9/2014 | Potter et al. |
| 2014/0299125 A1 | 10/2014 | Buchberger |
| 2014/0305449 A1 | 10/2014 | Plojoux et al. |
| 2014/0356607 A1 | 12/2014 | Woodcock |
| 2015/0027454 A1 | 1/2015 | Li et al. |
| 2015/0128973 A1 | 5/2015 | Li et al. |
| 2015/0196059 A1 | 7/2015 | Liu |
| 2015/0257447 A1 | 9/2015 | Sullivan |
| 2015/0264979 A1 | 9/2015 | Thorens et al. |
| 2015/0342256 A1 | 12/2015 | Chen |
| 2015/0374035 A1 | 12/2015 | Sanchez et al. |
| 2016/0020224 A1 | 1/2016 | Kawamura et al. |
| 2016/0073692 A1 | 3/2016 | Alarcon et al. |
| 2016/0120224 A1 | 5/2016 | Mishra et al. |
| 2016/0135505 A1 | 5/2016 | Li et al. |
| 2016/0143360 A1 | 5/2016 | Sanchez et al. |
| 2016/0174610 A1 | 6/2016 | Kuczaj |
| 2016/0227837 A1 | 8/2016 | Hammel et al. |
| 2016/0255879 A1 | 9/2016 | Paprocki et al. |
| 2016/0324216 A1* | 11/2016 | Li ................. A61M 11/042 |
| 2017/0042221 A1 | 2/2017 | England |
| 2017/0086506 A1* | 3/2017 | Rado ................. A24F 40/485 |
| 2017/0095624 A1 | 4/2017 | Davidson et al. |
| 2017/0143038 A1 | 5/2017 | Dickens |
| 2017/0156402 A1 | 6/2017 | Liu |
| 2017/0238612 A1 | 8/2017 | Daryani et al. |
| 2017/0251727 A1 | 9/2017 | Nielsen |
| 2017/0347706 A1 | 12/2017 | Aoun et al. |
| 2018/0027882 A1 | 2/2018 | Hepworth et al. |
| 2018/0235276 A1 | 8/2018 | Zuleta et al. |
| 2018/0325174 A1 | 11/2018 | Sutton |
| 2018/0360122 A1 | 12/2018 | Aoun et al. |
| 2018/0368478 A1 | 12/2018 | Golovanova et al. |
| 2019/0230990 A1 | 8/2019 | Hepworth |
| 2019/0254343 A1 | 8/2019 | Hepworth |
| 2019/0320718 A1 | 10/2019 | Yilmaz |
| 2019/0320725 A1 | 10/2019 | England |

FOREIGN PATENT DOCUMENTS

| | | |
|---|---|---|
| CA | 885796 A | 11/1971 |
| CA | 2330782 A1 | 7/2002 |
| CA | 2925645 A1 | 4/2015 |
| CA | 2940842 A1 | 9/2015 |
| CN | 1054887 A | 10/1991 |
| CN | 101433818 A | 5/2009 |
| CN | 101557728 A | 10/2009 |
| CN | 102264249 A | 11/2011 |
| CN | 102834027 A | 12/2012 |
| CN | 103315402 A | 9/2013 |
| CN | 103892467 A | 7/2014 |
| CN | 203762287 U | 8/2014 |
| CN | 104068474 A | 10/2014 |
| CN | 104284606 A | 1/2015 |
| CN | 104302197 A | 1/2015 |
| CN | 204273243 | 4/2015 |
| CN | 204317492 U | 5/2015 |
| CN | 104770876 A | 7/2015 |
| CN | 204653789 U | 9/2015 |
| CN | 105357995 A | 2/2016 |
| CN | 105394816 A | 3/2016 |
| CN | 105792688 A | 7/2016 |
| CN | 105962423 A | 9/2016 |
| DE | 2940535 A1 | 10/1980 |
| EA | 019736 B1 | 5/2014 |
| EP | 0174645 A2 | 3/1986 |
| EP | 0254551 A1 | 1/1988 |
| EP | 0305788 | 3/1989 |
| EP | 0307118 A1 | 3/1989 |
| EP | 0352106 A2 | 1/1990 |

(56) References Cited

FOREIGN PATENT DOCUMENTS

| | | |
|---|---|---|
| EP | 0535695 A2 | 4/1993 |
| EP | 0585016 A1 | 3/1994 |
| EP | 0845220 A1 | 6/1998 |
| EP | 1468618 A1 | 10/2004 |
| EP | 2489391 A1 | 8/2012 |
| EP | 2625974 A1 | 8/2013 |
| EP | 2625975 A1 | 8/2013 |
| EP | 2787848 A1 | 10/2014 |
| EP | 3127443 A1 | 2/2017 |
| GB | 2529201 A | 2/2016 |
| JP | S4742449 Y1 | 12/1972 |
| JP | S488231 B1 | 3/1973 |
| JP | S48008231 B | 3/1973 |
| JP | S60237982 A | 11/1985 |
| JP | S63193499 U | 12/1988 |
| JP | H0664983 A | 3/1994 |
| JP | 2001120250 A | 5/2001 |
| JP | 2009191148 A | 8/2009 |
| JP | 2010506594 A | 3/2010 |
| JP | 2012506263 A | 3/2012 |
| JP | 5247711 B2 | 7/2013 |
| JP | 2013545474 A | 12/2013 |
| JP | 2014511175 A | 5/2014 |
| JP | 2014520542 A | 8/2014 |
| JP | 2014529996 A | 11/2014 |
| JP | 2015504667 A | 2/2015 |
| JP | 2015509718 A | 4/2015 |
| JP | 5714637 B2 | 5/2015 |
| JP | 2015513393 A | 5/2015 |
| JP | 2017511703 A | 4/2017 |
| JP | 2017529896 A | 10/2017 |
| KR | 20120053521 A | 5/2012 |
| KR | 20130052119 | 5/2013 |
| KR | 20140118982 A | 10/2014 |
| RU | 122254 U1 | 11/2012 |
| RU | 2570499 C2 | 12/2015 |
| WO | WO-9748293 A1 | 12/1997 |
| WO | WO-9748296 A1 | 12/1997 |
| WO | WO-9828994 A1 | 7/1998 |
| WO | WO-0130184 A1 | 5/2001 |
| WO | WO-03008068 A1 | 1/2003 |
| WO | WO-03034847 A1 | 5/2003 |
| WO | WO-03056949 A1 | 7/2003 |
| WO | WO-2004086888 A2 | 10/2004 |
| WO | WO-2004087309 A1 | 10/2004 |
| WO | WO-2006048766 A1 | 5/2006 |
| WO | WO-2006070291 A2 | 7/2006 |
| WO | WO-2006072889 A1 | 7/2006 |
| WO | WO-2006089404 A1 | 8/2006 |
| WO | WO-2006097852 A1 | 9/2006 |
| WO | WO-2006103404 A1 | 10/2006 |
| WO | WO-2006109189 A1 | 10/2006 |
| WO | WO-2007031876 A2 | 3/2007 |
| WO | WO-2007036814 A2 | 4/2007 |
| WO | WO-2007069093 A2 | 6/2007 |
| WO | WO-2008108889 A1 | 9/2008 |
| WO | WO-2012106739 A1 | 8/2012 |
| WO | WO-2012168699 A1 | 12/2012 |
| WO | WO-2013034458 A1 | 3/2013 |
| WO | WO-2013083638 A1 | 6/2013 |
| WO | WO-2013098405 A2 | 7/2013 |
| WO | WO-2013102309 A1 | 7/2013 |
| WO | WO-2013116558 A1 | 8/2013 |
| WO | WO-2013120565 A2 | 8/2013 |
| WO | WO-2013155645 A1 | 10/2013 |
| WO | WO-2013164705 A1 | 11/2013 |
| WO | WO-2014116974 A1 | 7/2014 |
| WO | WO-2014136872 A1 | 9/2014 |
| WO | WO 2014139611 | 9/2014 |
| WO | WO-2014140273 A2 | 9/2014 |
| WO | WO-2014140320 A1 | 9/2014 |
| WO | WO-2014150773 A1 | 9/2014 |
| WO | WO-2014159250 A1 | 10/2014 |
| WO | WO 2015046385 | 4/2015 |
| WO | WO-2015062983 A2 | 5/2015 |
| WO | WO-2015091258 A1 | 6/2015 |
| WO | WO-2015128499 A1 | 9/2015 |
| WO | WO-2015179388 A1 | 11/2015 |
| WO | WO-2015188348 A1 | 12/2015 |
| WO | WO 2016024083 | 2/2016 |
| WO | WO-2016062777 A1 | 4/2016 |
| WO | WO-2016075748 A1 | 5/2016 |
| WO | WO-2016121143 A1 | 8/2016 |
| WO | WO-2016124740 A1 | 8/2016 |
| WO | WO-2016124741 A1 | 8/2016 |
| WO | WO-2016135331 A1 | 9/2016 |
| WO | WO-2016135342 A2 | 9/2016 |
| WO | WO-2016135342 A3 | 10/2016 |
| WO | WO-2016179376 A1 | 11/2016 |

OTHER PUBLICATIONS

Written Opinion, Application No. PCT/EP2016/073472, dated Jan. 31, 2017, 8 pages.
Application and File History for U.S. Appl. No. 15/521,082, filed Apr. 21, 2017, Inventor Aoun.
Application and File History for U.S. Appl. No. 15/553,742, filed Aug. 25, 2017, Inventor Turner.
Application and File History for U.S. Appl. No. 15/553,785, filed Aug. 25, 2017, Inventor Hepworth.
Application and Filing History for U.S. Appl. No. 16/058,604, filed Aug. 8, 2018, Inventors Aoun et al.
Communication pursuant to Article 94(3) EPC for Application No. 15793718.6, dated Dec. 20, 2018, 5 pages.
Communication pursuant to Article 94(3) EPC for Application No. 15793718.6, dated Apr. 1, 2020, 13 pages.
Communication pursuant to Article 94(3) EPC for Application No. 16709731.0, dated Sep. 30, 2019, 28 pages.
Communication pursuant to Article 94(3) EPC for Application No. 18190846.8, dated Apr. 1, 2020, 5 pages.
Definition of "Throughout," the Free Merriam-Webster Dictionary, Retrieved from http://www.merriam-webster.com/dictionary/throughout, Jun. 11, 2018, 15 pages.
European Search Report for Application No. EP18190846 dated Dec. 21, 2018, 10 pages.
Examination Report dated May 11, 2018 for Australian Application No. 2015334902, 5 pages.
Examination Report dated Apr. 14, 2020 for Australian Application No. 2019200330, 7 pages.
Examination Report dated Dec. 22, 2017 for Australian Application No. 2015334902, 3 pages.
International Preliminary Report on Patentability for Application No. PCT/EP2015/074395, dated May 1, 2017, 7 pages.
International Preliminary Report on Patentability for Application No. PCT/EP2016/054159, dated Jul. 14, 2017, 7 pages.
International Preliminary Report on Patentability for Application No. PCT/EP2016/054232, dated Jul. 3, 2017, 28 pages.
International Preliminary Report on Patentability for Application No. PCT/GB2012/051257, dated Jul. 12, 2013, 20 pages.
International Preliminary Report On Patentability for Application No. PCT/EP2016/073472, dated Apr. 3, 2018, 9 pages.
International Search Report and Written Opinion for Application No. PCT/GB2012/051257, dated Sep. 17, 2012, 22 pages.
International Search Report for Application No. PCT/EP2015/074395, dated Feb. 1, 2016, 2 pages.
International Search Report for Application No. PCT/EP2016/054159, dated Jun. 9, 2016, 3 pages.
International Search Report for Application No. PCT/EP2016/054232, dated Aug. 24, 2016, 5 pages.
International Search Report for Application No. PCT/GB2015/051253, dated Nov. 16, 2015, 6 pages.
International Written Opinion for Application No. PCT/EP2016/054159, dated Jun. 9, 2016, 7 pages.
International Written Opinion for Application No. PCT/EP2016/054232, dated Aug. 24, 2016, 8 pages.
Jac Vapour, "Round Rubber Mouth Tips," JAC Vapour E-Cigarettes & E-Liquids, retrieved from http://www.jacvapour.com/round-rubber-e-cig-mouth-tips on May 29, 2015, 2 pages.

(56) References Cited

OTHER PUBLICATIONS

Office Action and Search Report dated Feb. 3, 2020 for Chinese Application No. 201680056939.7, 20 pages.
Office Action dated Sep. 12, 2019 for Chinese Application No. 201680024542.X, 49 pages.
Office Action dated Sep. 12, 2019 for Chinese Application No. 201680024577.3, 21 pages.
Office Action dated Mar. 16, 2018 for Canadian Application No. 2963957, 4 pages.
Office Action dated Jul. 2, 2018 for Chinese Application No. 201580023549.5, 23 pages.
Office Action dated Jul. 2, 2018 for Chinese Application No. 201580023949.5, 23 pages.
Office Action dated Jan. 21, 2020 for Japanese Application No. 2018-515290, 4 pages.
Office Action dated Mar. 23, 2020 for Brazilian Application No. 112017018446.0, 8 pages.
Office Action dated Apr. 25, 2018 for Korean Application No. 10-2017-7013874, 16 pages.
Office Action dated Apr. 26, 2016 for Korean Application No. 10-2017-7027341, 14 pages.
Office Action dated Oct. 30, 2018 for Japanese Application No. 2017-545245, 22 pages.
Office Action dated Oct. 30, 2018 for Korean Application No. 1020177013874, 19 pages.
Office Action dated Feb. 5, 2019 for Japanese Application No. 2017-522122, 14 pages.
Office Action dated Nov. 6, 2018 for Japanese Application No. 2017-545230, 10 pages.
Office Action dated May 7, 2019 fo Japanese Application No. 2018-515290, 8 pages.
Partial International Search Report for Application No. PCT/EP2016/054232, dated Jun. 22, 2016, 6 pages.
Search Report dated Mar. 21, 2016 for Great Britain Application No. 1517470.9, 4 pages.
Written Opinion for Application No. PCT/EP2015/074395, dated Feb. 1, 2016, 5 pages.
Written Opinion for Application No. PCT/GB2015/051253, dated Nov. 16, 2015, 7 pages.
Written Opinion of the International Preliminary Examining Authority for Application No. PCT/GB2012/051257, dated May 29, 2013, 7 pages.
Application and File History for U.S. Appl. No. 14/124,637, filed Feb. 7, 2014, Inventor Branton, 468 pages.
Application and File History for U.S. Appl. No. 15/307,074, filed Oct. 27, 2016, Inventor England.
Office Action dated Aug. 24, 2020 for Chinese Application No. 201680056939.7, 33 pages.
Office Action dated May 15, 2018 for Japanese Application No. 2017-522122, 29 pages.
Office Action dated Jul. 30, 2019 for Japanese Application No. 2017-545230, 12 pages.
Search Report dated Apr. 23, 2015 for Great Britain Application No. 1418817.1, 5 pages.
European Search Report for European Application No. EP21166365.3, dated Jul. 21, 2021, 12 pages.
Examination Report for European Application No. 15725399.8, dated Jun. 4, 2019, 5 pages.
First Examination Report dated Dec. 11, 2019 for New Zealand Application No. 752875, 4 pages.
International Preliminary Report on Patentability for Application No. PCT/EP2017/077633, dated May 16, 2019, 7 pages.
International Search Report and Written Opinion for Application No. PCT/EP2017/077633, dated Feb. 5, 2018, 8 pages.
Merriam-Webster Dictionary, Definition of "throughout," the Free Merriam-Webster Dictionary, Mar. 7, 2015, http://www.merriam-webster.com/dictionary/throughout, 15 pages.
Notice of Reasons for Refusal for Japanese Application No. 2018-152380, dated Jun. 30, 2020, 22 pages.
Office Action for Canadian Application No. 3,042,128, dated Aug. 11, 2020, 6 pages.
Office Action for Chinese Application No. 201780067522.5, dated Jan. 8, 2021, 18 pages.
Office Action for Chinese Application No. 201780067522.5, dated Jan. 10, 2022, 6 pages.
Office Action for Japanese Application No. 2019-522376, dated Sep. 1, 2020, 9 pages.
Office Action dated Jun. 2, 2020 for Japanese Application No. 2017-545230, 5 pages.
Office Action dated Dec. 5, 2019 for Russian Application No. 2019116869, 13 pages.
Search Report For Russian Application No. 2018106929, dated Aug. 20, 2021, 2 pages.
Search Report dated Aug. 20, 2020 for Japanese Application No. 2019-522376, 36 pages.

\* cited by examiner

APPARATUS FOR GENERATING AN INHALABLE MEDIUM

PRIORITY CLAIM

The present application is a National Phase entry of PCT Application No. PCT/EP2016/073472, filed Sep. 30, 2016, which claims priority from GB Patent Application No. 1517471.7, filed Oct. 2, 2015, each of which is hereby fully incorporated herein by reference.

TECHNICAL FIELD

The present disclosure relates to an apparatus and methods for generating an inhalable medium.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are heating devices which release compounds by heating, but not burning, the material. The material may be for example tobacco or other non-tobacco products, which may or may not contain nicotine. As another example, there are so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain or use tobacco.

SUMMARY

According to a first aspect of the present disclosure, there is provided an apparatus for generating an inhalable medium, the apparatus comprising: a container for holding a liquid; a heater for volatilizing liquid held in the container to generate a flow of at least one of a vapor and an aerosol in use; and a receptacle for receiving material; wherein the receptacle is located adjacent to the heater such that in use, material received in the receptacle is heated by the heater, and wherein one or more constituents of material received in the receptacle in use are mixed with the flow of at least one of a vapor and an aerosol in use to produce the inhalable medium.

The apparatus may be arranged such that in use, the flow of at least one of a vapor and an aerosol passes through the material received in the receptacle in use, thereby to entrain the one or more constituents in the flow of at least one of a vapor and an aerosol.

The liquid container and the receptacle may be an integral unit.

The apparatus may comprise a gas inlet, and in use a gas flow from the gas inlet may pass through material received in the receptacle in use thereby to entrain the one or more constituents in the gas flow, and the gas flow having the one or more constituents entrained therein may be combined with the flow of at least one of a vapor and an aerosol in use.

The apparatus may be arranged such that the receptacle is intermediate to the gas inlet and the heater.

The receptacle may surround the heater.

The receptacle may be annular in shape.

The receptacle may comprise two or more discrete receiving portions each for receiving a respective discrete portion of material.

The liquid container may be removable from the apparatus.

The heater may heat the material received in the receptacle in use at least in part via one or both of radiation emitted from the heater and thermal conduction from the heater.

The heater may heat at least an outer portion of the material received in the receptacle in use to a temperature higher than an ambient temperature of the apparatus.

The heater may heat at least an outer portion of the material received in the receptacle in use to a temperature in the range 30° C. to 100° C.

The heater may heat at least an outer portion of the material received in the receptacle in use to a temperature in the range 40° C. to 80° C.

The receptacle may comprise one or more retainers for retaining material within the receptacle in use.

The one or more retainers may allow at least one of a vapor and an aerosol to pass there through, and prevent material received in the receptacle in use to pass there through.

The receptacle may have material received therein.

The material may be annular in shape.

The material may comprise a recess into which the heater may be at least partially inserted.

The material may be contained in a self-supporting material container.

The material may be material in solid form.

The material in solid form may be or may comprise tobacco.

The solid material may be or may comprise a flavored material.

According to a second aspect of the present disclosure, there is provided a method of generating an inhalable medium using an apparatus comprising a container for holding a liquid, a heater for volatizing the liquid, and a receptacle for receiving material, the method comprising: volatizing, using the heater, liquid held in the container to generate a flow of at least one of a vapor and an aerosol; heating, using the heater, material received in the receptacle; and mixing one or more constituents of the material with the flow of at least one of a vapor and an aerosol to produce the inhalable medium.

According to a third aspect of the present disclosure, there is provided a cartridge for use with an apparatus for generating an inhalable medium, the cartridge comprising: a container for holding a liquid; a heater for volatilizing liquid held in the container to generate a flow of at least one of a vapor and an aerosol in use; and a receptacle for receiving material; wherein the receptacle is located adjacent to the heater such that in use, material received in the receptacle is heated by the heater, and wherein one or more constituents of material received in the receptacle in use are mixed with the flow of at least one of a vapor and an aerosol in use to produce the inhalable medium.

According to a fourth aspect of the present disclosure, there is provided an atomizer for use with an apparatus for generating an inhalable medium, the atomizer comprising: a heater for volatilizing liquid to generate a flow of at least one of a vapor and an aerosol in use; and a receptacle for receiving material; wherein the receptacle is located adjacent to the heater such that in use, material received in the receptacle is heated by the heater, and wherein one or more constituents of material received in the receptacle in use are mixed with the flow of at least one of a vapor and an aerosol in use to produce the inhalable medium.

Further features and advantages of the disclosure will become apparent from the following description of preferred embodiments of the disclosure, given by way of example only, which is made with reference to the accompanying drawings.

DETAILED DESCRIPTION

Figure 1:
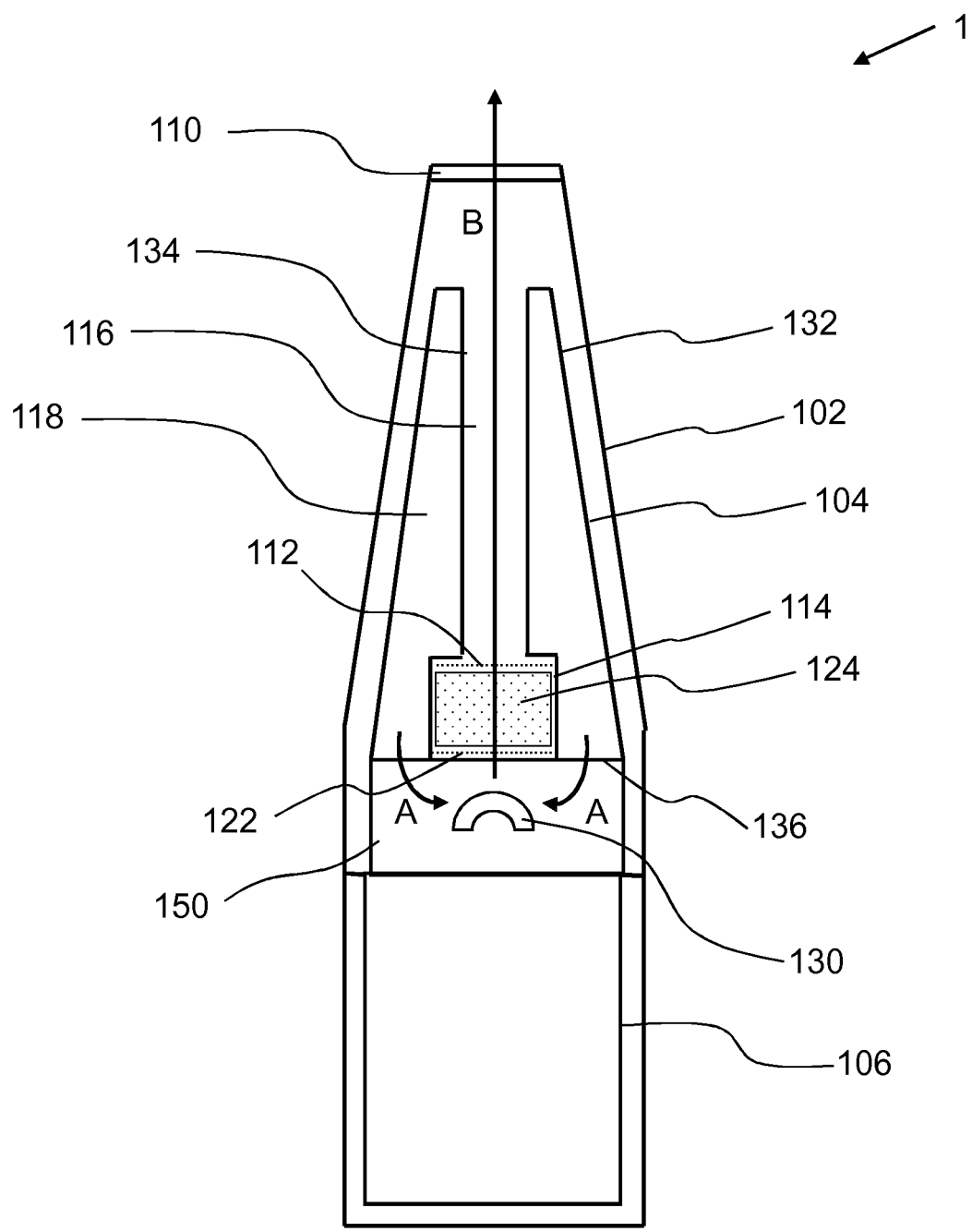
FIG. 1 shows a schematic cross section of an exemplary apparatus.

Referring to FIG. 1, a schematic cross section of an example of an apparatus 1 for generating an inhalable medium is illustrated. In broad outline, the apparatus 1 volatilizes a liquid to form a vapor or an aerosol which passes through a solid material so as to produce an inhalable medium that contains one or more constituents derived from the material.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A "colloid" is a substance in which microscopically dispersed insoluble particles are suspended throughout another substance.

Returning to FIG. 1, the apparatus 1 comprises an outer body 102 which houses a cartridge 104, a battery 106, and a mouthpiece 110 on which a user can draw. The cartridge 104 is connected to, but removable from, the battery 106. At least a portion of the outer body 102 may be removed so as to expose the cartridge 104, and hence allow installation, removal and/or replacement of the cartridge 104. The cartridge 104 has a liquid container 132 for containing liquid 118 and a receptacle 114 which has received therein solid material 124.

The solid material 124 may be for example tobacco, or other flavored materials that may be used to create a desired taste or aroma, or other properties, such as nicotine content.

In the example of FIG. 1, the receptacle 114 is generally cylindrical in shape and is integral to the liquid container 132. The receptacle 114 comprises a first retainer 122 and a second retainer 112 to retain the solid material 124 within the receptacle 114. The first and second retainers 112, 122 are permeable so as to allow gas phase material, such as vapor or an aerosol, to pass through, but to prevent material in the solid phase, such as solid material 124 from passing through. For example, the first and second retainers 112, 122 may comprise a mesh made from metal or plastic or ceramic or rubber or the like, or a permeable membrane, or simply a disc with holes running there through. In some examples, it may be useful that a retainer close to the heater 130, for example the first retainer 122 as shown in FIG. 1, is made from a heat resistant material and/or a material with high thermal conductivity. The retainers 112, 122 may be integral to the receptacle 114, and hence may be integral to the liquid container 132 (or cartridge 104) itself. In examples where the liquid container 132 is removable from the apparatus 1, one or more of the retainers 112, 122, for example the first retainer 122, may be removable so as to allow access to the receptacle 114 and hence allow a user to add, remove, or exchange the solid material 114 received therein.

In the example of FIG. 1, the cartridge 104 is arranged so that as the liquid 118 is volatilized so as to produce an aerosol of liquid droplets or sufficiently heated to produce a vapor, at least some and preferably all or substantially all of the aerosol or vapor passes through the solid material 124 for example so as to pick up flavor from the solid material 124.

In this example, the liquid container 132 is provided generally centrally of the cartridge 104. The liquid container 132 in the example shown is frustoconical in shape, but may have a different shape, such as conical, cylindrical, etc. The liquid container 132 is annular in shape and its inner wall 134 defines a cylindrical channel 116 running through the length of the liquid container 132 which extends from one end of the liquid container to the other. The liquid container 132 may be formed of rigid, watertight and airtight materials, such as metal, suitable plastics, etc.

The cartridge 104 is provided with a heater 130 and a wick (not shown) in (thermal) contact with the heater 130. In this example, the heater 130 and the wick are provided as a single unit 150, sometimes known as an "atomizer" 150. In this case, where the cartridge 104 includes an atomizer 150, such a cartridge 104 is often referred to as a "cartomizer" 104. The orientation of the heater 130 is shown schematically and for example the heater 130 may be a coil having its longitudinal axis perpendicular or parallel to the longitudinal axis of the cartridge 104. The wick (not shown) is in contact with the liquid 118. This may be achieved by for example the wick (not shown) being inserted through a through hole (not shown) in an end wall 136 of the liquid container 132. Alternatively or additionally, the end wall 136 may be a porous member which allows liquid to pass through from the liquid container 132, and the wick (not shown) may be in contact with the porous end wall 136. The end wall 136 may be for example in the form of a porous ceramic disk. A porous end wall 136 of this type helps to regulate the flow of liquid onto the wick (not shown). The wick is generally absorbent and acts to draw in liquid 118 from the liquid container 132 by capillary action (shown in FIG. 1 by arrows A). The wick can be non-woven and may be for example a cotton or wool material or the like, or a synthetic material, including for example polyester, nylon, viscose, polypropylene or the like, or a ceramic material.

In this example, the cartridge 104 is connected to the battery 106 to enable the heater 130 to be powered. When the heater 130 is powered (which may be instigated for example by the user operating a button of the apparatus 1 or by a puff detector of the overall apparatus, as is known per se), liquid 118 is drawn in from the liquid container 132 by the wick (shown in FIG. 1 as arrows A) and is heated by the heater 130 to volatilize or vaporize the liquid, so as to generate a flow of at least one of a vapor and an aerosol. As the user draws on the mouthpiece 110, air is drawn through an air inlet (not shown). The liquid 118 is volatized or vaporized by the heater 130 into air from the air inlet (not shown) thereby to produce one of a vapor and an aerosol.

The vapor or aerosol is drawn towards the first retainer 122 of the receptacle 114, and through the solid material 124 as shown by arrow B. The vapor or aerosol picks up (entrains) flavor (and/or other constituents) from the solid material 124. One or more constituents of the solid material 124 is thereby mixed with the flow of at least one of a vapor and an aerosol. In examples where the solid material 124 contains or includes nicotine, the vapor or aerosol may also contains nicotine entrained from that solid material. The vapor or aerosol passes through the second retainer 112 into the cylindrical channel 116 inside the length of the liquid container 132 as shown by arrow B, before exiting through the mouthpiece 110 (as shown by arrow B) for inhalation by a user. A one way valve (not shown) may be provided at or near the mouthpiece 110 so that the vapor or aerosol can only exit the cartridge 104 and cannot back-flow to the heater 130 or the electronics (not shown) of the apparatus 1.

In this example, the solid material 124 is not removable from the receptacle 114, and the cartridge 104 is disposable.

The material 124 is a material that may be used to impart a flavor (and/or one or more other constituents of the solid material 124) to the aerosol or vapor produced from the liquid 118 as the aerosol or vapor passes through the material 124. In some examples, the one or more constituents of the solid material 124 may comprise constituents inherent to the solid material itself. The material 124 may for example consist of or comprise tobacco. As the aerosol or vapor passes through and over the tobacco material 124, the hot aerosol or vapor entrains organic and other compounds or constituents from the tobacco material that lend tobacco its organoleptic properties, thus imparting the flavor to the aerosol or vapor as it passes to the mouthpiece 110. It will be understood however that materials other than tobacco may be used to impart different flavors (and/or one or more other constituents) to the aerosol or vapor stream. The one or more constituents of the solid material 124 may comprise constituents added to the solid material 124. For example, flavorants could be included in the material or in the liquid. In addition, where the material 124 is or includes tobacco, it may be that the aerosol or vapor stream draws sufficient nicotine from the tobacco material 124.

Alternatively or additionally, where the material 124 does not contain any tobacco, nicotine may be provided in the liquid 118. Accordingly, where it is intended that the apparatus 1 provides nicotine for the user, the nicotine may be provided in the liquid 118, may be obtained from the material 124 in the case that the material is or includes tobacco, or any combination of these. Likewise, flavorings may be added to the material 124 (whether or not the material is or includes tobacco) and/or to the liquid 10. The solid material 124 may itself be a mixture of solid materials, one or more of each comprising one or more constituents that can be mixed with the flow of vapor or aerosol. It will be appreciated that the solid material 124 may comprise one or more other constituents that are not entrained into the aerosol or vapor passing there through.

In this example, the receptacle 114, and hence the solid material 124 received therein, is adjacent to the heater 130.

The placement of the receptacle 114 and hence the material 124 adjacent to the heater 130 allows the material 124 to be heated by the residual heat of the heater 130. For example, the heater 130 may heat the receptacle 114 and the material 124 received therein via radiation (in particular infrared radiation) emitted by the heater 130 (or components thereof) falling directly on the receptacle 114 (or a portion thereof) or a retainer 122 of the receptacle 114, or directly on the solid material 124 itself (for example via perforations in the retainer 122). The heater 130 may alternatively or additionally heat the receptacle 114 and the material 124 received therein by thermal conduction from the heater 130 (and/or any surrounding components thereof) to the receptacle 114. The thermal conduction to the receptacle 114 may be via intermediate components between the heater 130 and the receptacle 114. It may be preferable that the receptacle 114 and/or components between the receptacle 114 and the heater 130 (for example, the retainer 122) comprise good thermal conductors, for example, copper or other metals, non-metals such as graphene or other carbon based materials. There may also be provided a dedicated thermal conduction component (not shown) connecting the heater or a component thereof to the receptacle or directly to the solid material 124 to ensure good thermal conduction of heat from the heater 130 to the receptacle 114 and/or the material 124 received therein. The receptacle 114, being heated by the heater 130, in turn heats the solid material 124 received therein by for example, thermal conduction, radiation, convection, or any combination thereof. In this case, the heater 130 heats the material 124 via the receptacle 114.

The material 124 being heated by the heater 130 encourages release of constituents from the material 124. In the example that the material 124 is or comprises tobacco, heating of the tobacco (for example above ambient temperature) increases the release of volatile constituents of the tobacco, thereby increasing the level of flavor imparted to, for example, vapor and/or aerosol passing there through. The heating of the material 124 by the heater 130 that volatizes the liquid 118 reduces a need to provide a separate, dedicated, heater to heat the material 124, and hence the electricity required to power the device may be reduced, and hence battery life may be preserved.

Moreover, vapor or aerosol adjacent to the heater may have a temperature higher than vapor or aerosol that has travelled away from the heater. The temperature of the vapor or aerosol adjacent to the heater may therefore be higher than the ambient temperature of the material 124. The receptacle 114 and hence the material 124 being placed adjacent to the heater 130 may therefore allow the vapor or aerosol passing through the solid material to contribute to the heating of the solid material 124. This may improve release of constituents from the solid material 124 into the vapor or aerosol passing there through.

In the above example, the receptacle 114 formed part of the liquid container 132. In other examples, the receptacle 114 may be placed in other portions of the cartridge 104, such as within the atomizer 150.

Figure 2:
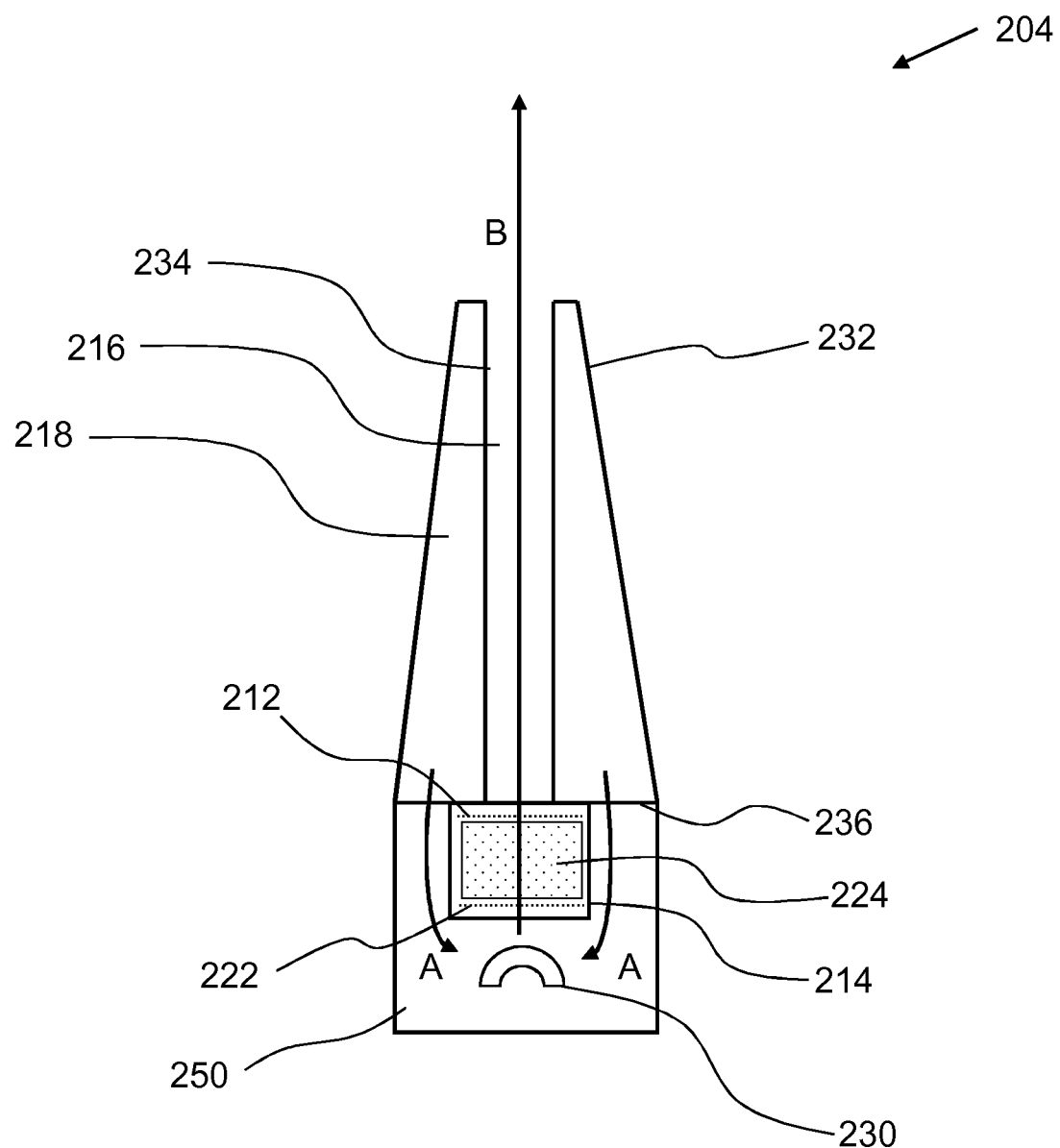
FIG. 2 shows a schematic cross section of an exemplary cartridge.

FIG. 2 illustrates a schematic cross section of an example cartridge 204 that can be used, for example, in apparatus 1 of FIG. 1 instead of cartridge 104. For brevity, features in FIG. 2 that are the same or similar to those features already described with reference to FIG. 1 are given similar reference numerals to as in FIG. 1 but increased by 100, and will not be described in detail again. The main difference of the cartridge 204 in FIG. 2 with respect to the cartridge 104 in FIG. 1 is that in the cartridge 204 of FIG. 2 the receptacle 214 is positioned within the atomizer 250, whereas in the cartridge 104 of FIG. 1 the receptacle 114 is positioned within the liquid container 132.

Referring now to the example of FIG. 2, the cartridge 204 comprises an atomizer 250 and a liquid container 232 for containing liquid 218. The liquid container 232 is annular in shape and its inner wall 234 defines a cylindrical channel 216 running through the length of the liquid container 232 which extends from one end of the liquid container 232 to the other. The atomizer 250 has a receptacle 214 which has received therein solid material 224. The atomizer 250 is provided with a heater 230 and a wick (not shown) in (thermal) contact with the heater 230, and in contact with the liquid 218. The wick acts to draw in liquid 218 from the liquid container 232 (shown in FIG. 2 by arrows A). The receptacle 214 comprises a first retainer 222 and a second retainer 212 to retain the solid material 224 within the receptacle 214.

In the example of FIG. 2, the receptacle 214 is located within and is integral to the atomizer 250. The retainers 212, 222 may be integral to the receptacle 214, and hence may be integral to the atomizer 250 (or cartridge 204) itself. In the case that the liquid container 232 is not removable from the atomizer 250 (i.e. the cartridge 204 is a "cartomizer", the cartridge 204 may be disposable. In examples where the atomizer 250 is removable from the liquid container 232, one or more of the retainers 212, 222, for example, the second retainer 212, may be removable from the atomizer 250 so as to allow access to the receptacle 214, and hence allow a user to add, remove, or exchange the material 224 received therein. Optionally, the first retainer 212 (i.e. the upper retainer as drawn in FIG. 2) may be omitted such that material 224 is held in the receptacle 214 by only the second retainer 222 (i.e. the lower retainer as drawn in FIG. 1) and, for example, gravity, and/or liquid container 232. The material 224 may be, for example, loose material such as tobacco that may be placed in and removed from the receptacle 214. The material 224 may be formed so as to be self-supporting, for example a plug or rod of tobacco or the like, that may be placed in and removed from the receptacle 214. The material 224, whether self-supporting or not, may be received in a self-supporting container (not shown) that is permeable to vapor or aerosol. The container 224 may be placed in and removed from the receptacle 214. The container (not shown) may be made, for example, from a heat resistant material and/or a material with high thermal conductivity.

In this example, liquid 218 drawn in from the liquid container 232 by the wick (shown in FIG. 1 as arrows A) and is heated by the heater 230 to volatilize or vaporize the liquid 218 into air from an inlet (not shown) so as to generate a flow of at least one of a vapor and an aerosol. The vapor or aerosol is drawn towards the first retainer 222 of the receptacle 214, and through the solid material 224 as shown by arrow B. The vapor or aerosol picks up (entrains) flavor (and/or other constituents) from the solid material 224. Constituents of the material are therefore mixed with the flow of at least one of a vapor and an aerosol to generate the inhalable medium. The vapor or aerosol passes through the second retainer 212 into the cylindrical channel 216 inside the length of the liquid container 232 as shown by arrow B, before exiting for inhalation by a user.

In this example, the receptacle 214, and hence the solid material 224 received therein, is adjacent to the heater 230 of the atomizer 250. Similarly to as described above with reference to FIG. 1, the placement of the receptacle 214 and hence the material 224 adjacent to the heater 230 in the atomizer 250 ensures that the vapor or aerosol passing through the material 224 is still at an elevated temperature, and allows the material 224 to be heated by the residual heat of the heater 230 itself. This encourages release of constituents from the material 224 and hence provides similar power consumption and liquid usage reductions as described above.

In the above examples, the cartridge 104, 204 was arranged such that the receptacle 114, 214 was placed downstream of the heater 130, and hence the liquid volatized by the heater 130, 230 (flowing in the form of at least one of a vapor and an aerosol) passed through the solid material 124, 224 received in the receptacle 114, 214 before being inhaled by a user. However, in other examples, the receptacle, and hence the solid material received therein, is upstream of the heater, and liquid volatized by the heater flowing as one of a vapor and an aerosol is mixed with a gas flow that has passed through solid material received in the receptacle.

Figure 3:
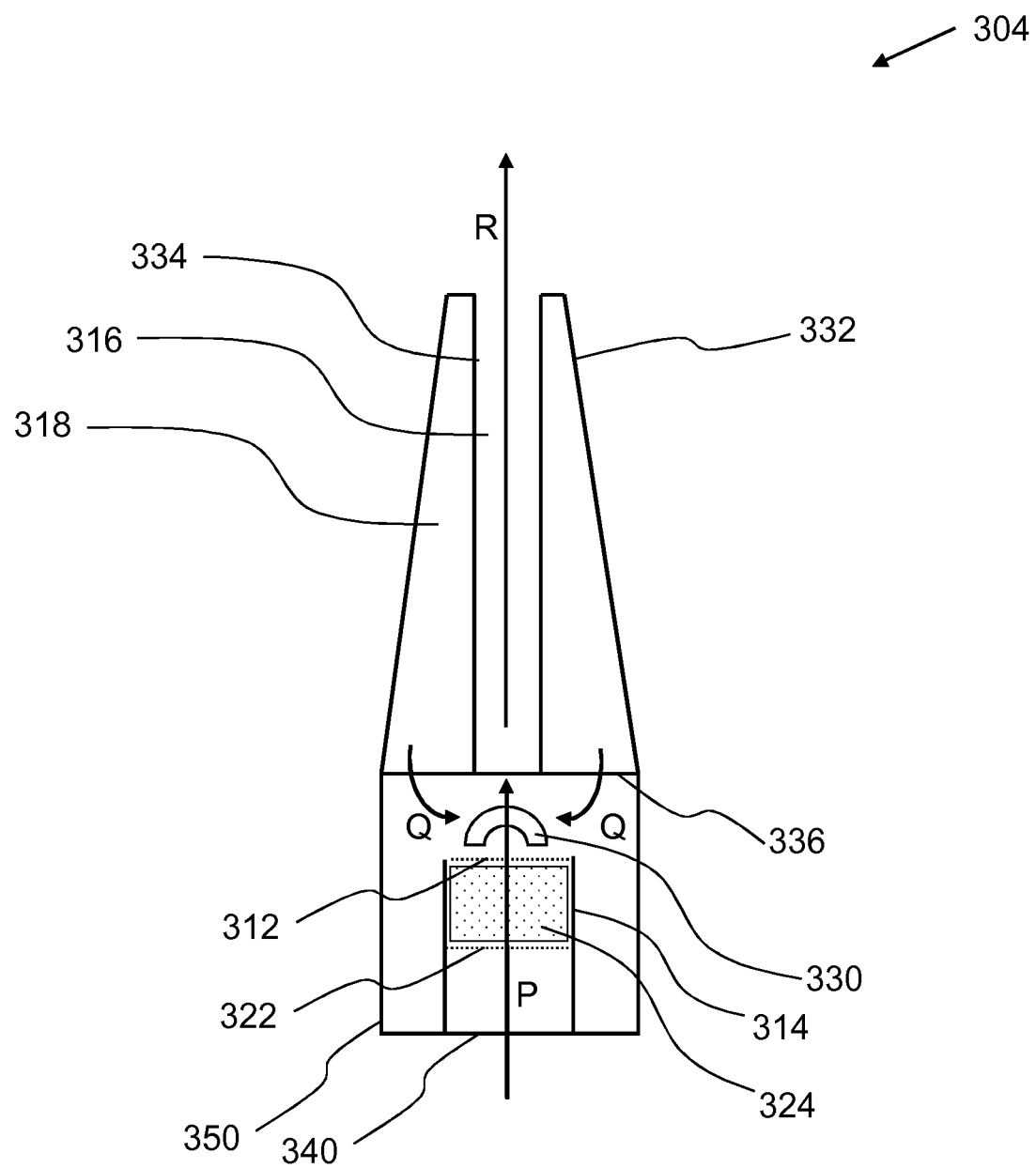
FIG. 3 shows a schematic cross section of an exemplary cartridge.

FIG. 3 illustrates a schematic cross section of another example cartridge 304 that may be used in apparatus 1 of FIG. 1 instead of the cartridge 104 in FIG. 1. For brevity, features in FIG. 3 that are the same or similar to those features already described with reference to FIG. 2 (and hence FIG. 1) are given similar reference numerals to as in FIG. 2 but increased by 100, and will not be described in detail again. The main difference of the cartridge 304 in FIG. 3 with respect to the cartridge 204 in FIG. 2 is that in the cartridge 304 of FIG. 3 the receptacle 314 is positioned upstream of the heater 330, whereas in the cartridge 204 of FIG. 2 the receptacle 214 is located downstream of the heater 230.

Referring now to the example of FIG. 3, similarly to as in the examples described above with reference to FIGS. 1 and 2, the cartridge 304 comprises an atomizer 350 and a liquid container 332 for containing liquid 318. The liquid container 332 is annular in shape and its inner wall 334 defines a cylindrical channel 316 running through the length of the liquid container 332 which extends from one end of the liquid container 332 to the other. The atomizer 350 has a receptacle 314 which has received therein solid material 324. The atomizer 350 is provided with a heater 330 and a wick (not shown) in (thermal) contact with the heater 330, and in contact with the liquid 318. The wick acts to draw in liquid 318 from the liquid container 332 (shown in FIG. 3 by arrows Q). The receptacle 314 comprises a first retainer 322 and a second retainer 312 to retain the solid material 324 within the receptacle 314.

In this example, the atomizer 350 has a gas inlet 340 to allow a gas, for example, air, into the atomizer 350. In this example, the receptacle 314 is integral to the atomizer 350, and the receptacle 314 is upstream of the heater 330. In this example, the receptacle 314 is integral to inlet 340. The retainers 312, 322 may be integral to the receptacle 314, and hence may be integral to the atomizer 350 (or cartridge 304) itself. In such cases, the cartridge 304 may be disposable. In examples where one or more of the retainers 312, 322, for example, the second retainer 312, are removable a user may access the receptacle 314, and hence add, remove, or exchange the material 324 received therein.

In this example, as a result of a user drawing on a mouthpiece (not shown in FIG. 3) of an overall apparatus (not shown in FIG. 3), gas, for example air, is drawn into inlet 340. The gas is drawn towards the first retainer 322 and passes through the solid material 324 received in the receptacle 314, thereby to entrain one or more constituents (for example, flavor) of the solid material 324 into the gas flow. The solid material 324 is adjacent to the heater 330 and hence is heated by the heater 330. The heating of the solid material 314 improves release of the constituents of the solid material 314 into the gas flow as compared to if the solid material 314 was not heated. The gas flow, having the one or more constituents entrained therein, is then drawn through the second retainer 312 and over (or near) heater 330 (shown in FIG. 3 by arrow P). Liquid 318 drawn in from the liquid container 332 by the wick (shown in FIG. 3 as arrows Q) and is heated by the heater 330 to volatilize the liquid 318 into a flow of at least one of a vapor and an aerosol. The vapor or aerosol flow is therefore mixed with the gas flow, having the one or more constituents entrained therein, to produce an inhalable medium. The mixture of flows then passes through the second retainer 312 into the cylindrical channel 316 inside the length of the liquid container 332 (shown in FIG. 3 shown as arrow R), before exiting for inhalation by a user.

In this example, the receptacle 314, and hence the solid material 324 received therein, is adjacent to the heater 330 of the atomizer 350. Similarly to as described above with reference to FIGS. 1 and 2, the placement of the receptacle 314 and hence the material 324 adjacent to the heater 330 in the atomizer 350 allows the material 324 to be heated by the residual heat of the heater 330 itself. This improves release of constituents from the material 324 into the gas flow, and hence the inhalable medium as compared to if the solid material was not heated. The heating of the material 324 by the heater 330 that volatizes the liquid 328 reduces the need to provide a separate heater to heat the material 324, and hence the electricity required to power the device may be reduced, and hence battery life may be preserved. Further, since the material 324 is heated by the heater 330 itself and the constituents thereof are entrained in a gas flow into which the vapor or aerosol is subsequently added, the temperature of the aerosol or vapor need not be relied upon itself to release constituents from the material 314. Moreover, in this example, the vapor or aerosol does not need to pass through the solid material 314 in order that the generated inhalable medium has constituents of the solid material 314 entrained therein. As a result, the vapor or aerosol is not filtered by the solid material 314, (i.e. has a clear flow path from the heater 330 to the mouthpiece (not shown in FIG. 3)). For a given heater 330 temperature and liquid 318 amount therefore, the vapor or aerosol yield exiting the cartridge 304 is therefore increased as compared with cases in which the aerosol or vapor must pass through the solid material. Alternatively, a reduced heater 330 temperature and/or liquid 318 amount can be used for a given yield of vapor or aerosol exiting the cartridge 304, and hence associated power and liquid consumption savings are provided.

In the above examples, the cartridge 104, 204, 304 was arranged such that the liquid container 132, 232, 323 was annular in shape and its inner wall 134, 234, 334 defined a cylindrical channel 136, 236, 336 running through the length of the liquid container 132, 232, 323. However, in other examples, the liquid container may not be annular in shape, and the cartridge may comprise an outer shell that defines an annular channel between the liquid container and the outer shell through which vapor or aerosol may pass for inhalation by the user.

Moreover, in the above examples, the receptacle 114, 214, 314 was generally cylindrical in shape, and the gas or vapor/aerosol flowed through the receptacle from one end of the receptacle 114, 214, 314 to the other. However, in other examples the receptacle may be annular, and the gas or aerosol/vapor may flow radially outwards (or inwards) through the receptacle, and hence the solid material received therein.

FIG. 4 illustrates a schematic cross section of an example cartridge 404 that can be used, for example, in apparatus 1 of FIG. 1 instead of cartridge 104. For brevity, features in FIG. 4 that are the same or similar to those features already described with reference to FIG. 3 (and hence FIGS. 1 and 2) are given similar reference numerals to as in FIG. 3 but increased by 100, and will not be described in detail again. The main difference of the cartridge 404 of FIG. 4 with respect to the other cartridges described above is that in the cartridge 430 of FIG. 4, the vapor or aerosol produced at the heater 430 flows radially out through an annular receptacle 414 containing a solid material 424 so as to entrain constituents of the solid material 424 into the vapor or aerosol flow. Moreover, in the cartridge 404 of FIG. 4, vapor or aerosol exiting the receptacle 414 flows through an annular channel 470 between the liquid container 432 and an outer shell 480, before flowing out of the cartridge 404 for inhalation by a user.

Referring to FIG. 4, a cartridge 404 comprises an atomizer 450 and a liquid container 432 for containing liquid 418. The atomizer 450 has an annular receptacle 414 which has received therein solid material 424. The atomizer 450 is provided with a heater 430 and a wick 490 in (thermal) contact with the heater 430, and in contact with the liquid 418. The wick 490 draws in liquid 418 from the liquid container 432 (shown in FIG. 4 by arrow X).

In this example, the receptacle 414 is generally annular in shape, is integral to the atomizer 450 and is downstream of the heater 430. The receptacle 414 is located such that the heater 430 is generally central of the receptacle 414, that is, the annular receptacle 414 surrounds the heater 430. The receptacle 414 comprises a first retainer 422 and a second retainer 412 to retain the solid material 124 within the receptacle 214. The first and second retainers 412, 422 are permeable so as to allow gas phase material, such as vapor or an aerosol, to pass through, but to prevent material in the solid phase, such as solid material 424 from passing through. The retainers 412, 422 may themselves be annular, or may only extend part way around the outer and inner walls of the annular receptacle 414. The retainers 412, 422 may be integral to the receptacle 414, and hence may be integral to the atomizer 450 (or cartridge 404) itself. The cartridge 404 may therefore be disposable. The receptacle 414 comprises a top wall 474 and a bottom wall 414 that, in addition to the retainers 412, 422, may hold the solid material in place within the receptacle 414. One or both of the top wall 474 and bottom wall 472 may be removable from the atomizer 450 so as to allow access to the receptacle 414, and hence allow a user to add, remove, or exchange the material 424 received therein. It will be appreciated that to be received in the annular receptacle, the solid material 424 may itself need to be annular in shape.

In this example, the liquid container 432 is not annular and is frustroconical in shape, but may be any other shape such as cylindrical or the like. The cartridge 404 comprises an outer shell 480 that is connected to the atomizer 450 and encases the liquid container 432. In this example, the outer shell is frustroconical in shape, but may be any shape, such as cylindrical etc. The liquid container 432 and the outer shell 432 define between them an annular channel 470 running the length of the liquid container 432.

In this example, liquid 418 is drawn in from the liquid container 432 by the wick 490 (shown in FIG. 4 as arrow X) and is heated by the heater 430 to volatilize or vaporize the liquid 418 into a flow of at least one of a vapor and an aerosol. The vapor or aerosol is drawn outwards from the heater 430 towards the first retainer 422 of the annular receptacle 414, and through the solid material 424 (shown in FIG. 4 by arrows Y). The vapor or aerosol picks up flavor (and/or other constituents) from the solid material 424. The vapor or aerosol passes through the second retainer 412 into the annular channel 470 defined between the outer shell 480 and the liquid container 432 (shown in FIG. 4 by arrows Y), before exiting for inhalation by a user (shown in FIG. 4 by arrow Z).

In this example, the annular receptacle 414, and hence the solid material 424 received therein, is adjacent to the heater 430 of the atomizer 450, and surrounds the heater 430. Similarly to as described above with reference to FIG. 1, the placement of the receptacle 414 and hence the material 424 adjacent to the heater 430 in the atomizer 450 allows the material 424 to be heated by the residual heat of the heater 430 itself. Moreover, since the vapor or aerosol adjacent to the heater may have a temperature higher the ambient temperature of the material 424, the vapor or aerosol passing through the solid material 424 may contribute to the heating of the material 424. Heating of the solid material 424 encourages release of constituents from the material 424 and hence provides similar improvements in constituent yield and/or power consumption reductions as described above. Moreover, the receptacle 414 surrounding the heater 430 as per this example enables the receptacle 414 to cover a larger proportion (i.e. a larger solid angle) of the space surrounding the heater 430, and hence to collect more residual heat of the heater 430. This further encourages release of constituents from the material 424 and hence provides similar improvements in constituent yield and/or power consumption reductions as described above.

Figure 4:
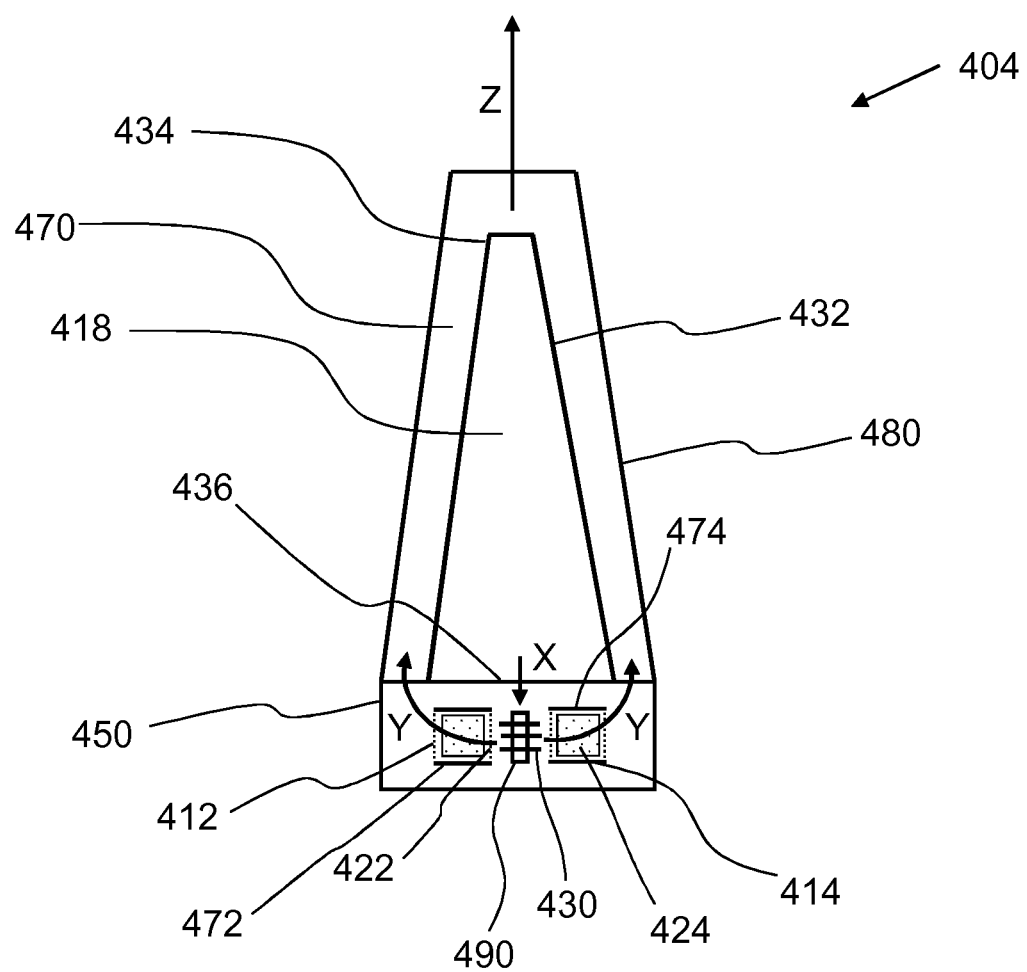
FIG. 4 shows a schematic cross section of an exemplary cartridge.
Figure 5:
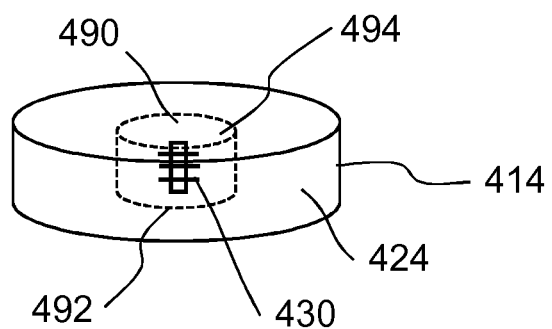
FIG. 5 shows schematically a perspective view of an exemplary receptacle.

FIG. 5 illustrates in more detail and in perspective view the annular shaped receptacle 414 and solid material 424 surrounding the heater 430 as illustrated in FIG. 4. The solid material 424 may comprise loose material which is formed into an annular shape by being received into an annular receptacle 414. Alternatively or additionally, the solid material 424 may be pre-formed to be annular in shape and so as to be a self-supporting. Alternatively or additionally, the solid material 424 may be contained in a self-supporting container (not shown) that is annular in shape and is permeable to vapor or aerosol, which container mat be placed in the receptacle 414. In any case, in the solid material 424 is generally disc shaped, and comprises a bore 494 along the principal axis of the disc that extends from a first opening 490 on one side of the disk, all the way through the solid material, to a second opening 492 on the opposite side of the disk. In use, the heater 430 sits substantially inside the bore 494. Residual heat from the heater 130 is collected from the surface of the solid material defined by the bore 494.

Although in FIGS. 4 and 5 the receptacle 414 and solid material 424 are annular in shape, this need not necessarily be the case. For example, the solid material may be generally disk shaped and comprise a recess into which the heater may be docked (i.e. at least partially inserted).

Figure 6:
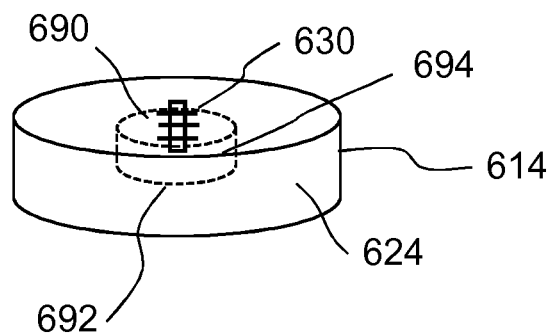
FIG. 6 shows schematically a perspective view of an exemplary receptacle.

FIG. 6 illustrates a perspective view of a disk shaped receptacle 624 and solid material 624 placed over a heater 630. The generally disk shaped solid material 624 comprises a recess 694 along the principal axis of the disc that extends from a first opening 690 on one side of the disk, part way through the solid material, to a closed end 692 located within the disk. In use, the heater 630 sits substantially inside the recess 694. Residual heat from the heater 130 is collected from the surface of the solid material defined by the recess 694, which includes closed end 692. In this case, a large solid angle of the area surrounding the heater 630 may be covered by the solid material 624, and hence a large proportion of the residual heat from the heater 630 may be collected by the solid material 624. The receptacle 614 into which the solid material 624 is received may be shaped accordingly. In examples where the solid material is pre-formed into a self-supporting structure, or where the solid material is itself contained in a self-supporting container (not shown), the structure of the recess 694 may be built into the solid material itself. In this case, the receptacle 614 need not provide the structure for the recess 694, and may be generally disk shaped. The receptacle 614 and/or the recessed solid material 624 illustrated in FIG. 6 may be used with, for example, the cartridge 404 shown in FIG. 4 in place of the receptacle 414 and/or annular solid material 424 shown therein, which cartridge 404 may in turn be used, for example, in the apparatus 1 shown in FIG. 1 in place of the cartridge 104 shown therein.

Although in FIGS. 4, 5 and 6 the receptacle 414, 614 and solid material 424, 624 were of a single and continuous shape, this need not necessarily be the case. For example, the receptacle may be formed of two or more discrete portions, and solid material may be received in either or both.

Figure 7:
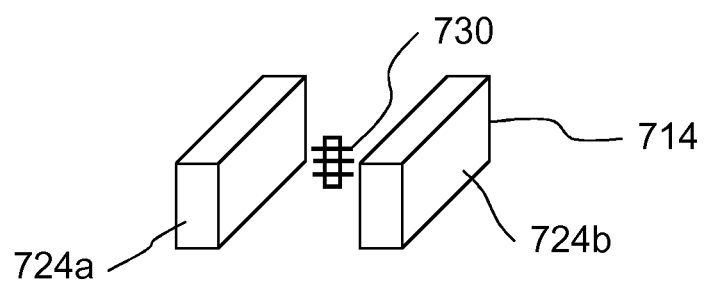
FIG. 7 shows schematically a perspective view of an exemplary receptacle.

FIG. 7 illustrates a perspective view of a receptacle 714 which has received therein two separate blocks of solid material 724a, 724b placed either side of a heater 730. In this example, the two blocks of solid material 724a, 724b are cuboidal. Each block 724a, 724b is positioned so that one of the faces of each block 724a, 724b with the largest surface area is facing the heater 730. The receptacle 714 into which the one or both of the blocks of solid material 724a, 724b may be received may be shaped so as to comprise two cuboidal recesses accordingly. In examples where the solid material 724a, 724b is pre-formed into a self-supporting structure, or where the solid material blocks 724a, 724b are themselves contained in self-supporting containers (not shown), the receptacle 714 may, for example, comprise one generally cuboidal recess into which the solid material blocks 724a, 724b may be placed. The receptacle 714 and/or the blocks of solid material 724a, 724b illustrated in FIG. 7 may be used with, for example, the cartridge 404 shown in FIG. 4 in place of the receptacle 414 and/or annular solid material 424 shown therein, which cartridge 404 may in turn be used, for example, in the apparatus 1 shown in FIG. 1 in place of the cartridge 104 shown therein.

Although in the above examples, the receptacle and/or solid material was described as being generally disk shaped, or generally annular, or generally cuboidal, it will appreciated that in some examples, any shaped volume may be used instead.

Although the examples above referred to use of a receptacle 114, 214 etc. with a cartridge 104, 204 etc., it will be readily appreciated that there are many configurations of so called e-cigarettes (some of which not having cartridges as such, but rather, for example, refillable chambers integral to the apparatus 1) and that the above examples may also be applied to these other configurations. Indeed, locating a receptacle 114, 214, etc. adjacent to a heater 130, 230 etc. for volatizing liquid 118, 218, etc. such that the heater 130, 230 etc. heats solid material 124, 224, etc. received in the receptacle 114, 214, etc., and mixing one of more constituents of the solid material 124, 224, etc. with a flow of vapor or aerosol as described above may be independent of the configuration or arrangement of the apparatus.

A number of other variations and alternatives to the examples described above are possible.

For example, in some cases it may be possible for the receptacle having solid material received therein to be located, exclusively or additionally, in the battery section 106, etc. with which the cartridge described above is used, provided that the receptacle is adjacent to the heater.

As another example, in cases where the solid material is removable from the receptacle, the solid material may be omitted from the receptacle, for example at the option of the user. This provides the user with more flexibility.

In some examples described above, the cartridge comprises an annular channel 470 that completely surrounds the liquid container 432. In other examples, the channel 470 is not annular and does not surround the liquid container 432. For example, the channel 470 may only partially surround the liquid container 432, and there may be multiple separate channels each only partly surrounding the liquid container 432.

In some of the examples above, the liquid container and the receptacle are arranged substantially in-line, along a longitudinal axis of the apparatus or cartridge. In other examples, the liquid container and the receptacle are arranged so as to at least partially overlap in the longitudinal direction of the apparatus or cartridge; in such examples, the liquid container and the receptacle may still be arranged generally in-line along the longitudinal axis of the apparatus or cartridge, or may be arranged side by side, or with one partially or completely inside the other. In yet other examples, the liquid container and the receptacle are arranged concentrically (either with the liquid container inside the receptacle or vice versa), and may be arranged to be entirely off-set with respect to each other along the longitudinal axis of the apparatus or cartridge, or overlapping, or one completely within the other.

The liquid is preferably a liquid that is volatilizable at reasonable temperatures, preferably in the range of 100-300° C. or more particularly around 150-250° C., as that helps to keep down the power consumption of the apparatus with which the cartridge is used. Suitable materials include those conventionally used in e-cigarette devices, including for example propylene glycol and glycerol (also known as glycerine). Also as described in relation to the examples above, the solid material is a material that may be used to impart a flavor (or other constituent) to the aerosol or vapor produced from the liquid as the aerosol or vapor passes through the material. For example, the material may comprise constituents that impart cooling sensations, heating sensations, neutraceutical benefits, stimulating benefits or produce or induce any other sensation or benefit in the user. The material may for example consist of or comprise tobacco. As the aerosol or vapor passes through and over the tobacco material, the aerosol or vapor entrains organic and other compounds or constituents from the tobacco material that lend tobacco its organoleptic properties, thus imparting the flavor to the aerosol or vapor as it passes to the mouthpiece. Materials other than tobacco may be used to impart different flavors to the aerosol or vapor stream. For example, materials other than tobacco may be blended with tobacco, or blends of other materials such as, for example, vanilla pods, star anise, mint leaves, other herbs, and the like. For example, flavorants could be included in the material or in the liquid or both.

In any of the examples described above, an apparatus controller may control operation of the apparatus as a whole. The controller for example may cause the heater to be powered as and when required and switch off the heater when heating is not required. Operation of the heater may be controlled so that the liquid and/or material is heated to an optimum temperature. Particular considerations include ensuring that the solid material does not burn, ensuring that adequate vaporization of the liquid is achieved, ensuring that the vaporized liquid or aerosol is at an appropriate temperature to liberate compounds from the solid material, and ensuring that the vapor or aerosol that reaches the user is at a comfortable and safe temperature. A puff detector, a device which is known per se, may be provided to signal to the controller when the heating elements need to be energized. Alternatively or additionally, the user may control the apparatus via controls or an interface external to the overall apparatus (not shown), for example via radio control signals, or Bluetooth or the like from a separate control device, such as a smartphone or the like. The apparatus may also have one or more filters for filtering the vapor or aerosol before it reaches the user, cooling arrangements for cooling the vapor or aerosol before it reaches the user, insulation internally of the apparatus to protect the user from the heat generated inside the housing, etc.

In use, and particularly in the case that the solid material is tobacco, it is preferred that the tobacco, or at least an outer portion or the surface of the tobacco (or other material), be heated to a temperature of between around 30° C. to 100° C. and most preferably between 40° C. and 80° C. so as to improve the release of constituents of the tobacco as compared to ambient temperatures. The material may be heated only by the heater or may be additionally heated by vapor or aerosol with a temperature higher than the temperature of the solid material that passes through the solid material. In the case of heating by the heater, the material, particularly in the case of tobacco, may be heated to a temperature in the range of around 40 to 80° C., although it will be appreciated that any temperature above ambient temperature of the material and/or above the ambient temperature of the apparatus as a whole will improve release of constituents from the solid material. It will be appreciated however that other temperatures may be used. For example, the solid material, or at least the surface of the material, may be heated to a temperature above 210° C., such as up to around 230° C. or 240° C. or so and even as high as 290° C. or so. The amount of tobacco present may be for example in the range 50 to 300 mg or so. A most suitable value for the amount of tobacco may be for example in the range 50 to 150 mg, with 130 mg being a value that is currently found to be particularly suitable in some applications. In a typical example, the amount of tobacco that is heated per operation of the apparatus (i.e. per puff) may be in the corresponding range of around 8 to 50 mg.

In use, the liquid may be heated to a temperature of between around 100-300° C. or more particularly around 150° C. to 250° C. Suitable liquid materials 118 etc. include materials that provide volatilized components upon heating, typically in the form of an aerosol. Suitable solid materials 124 etc. include any tobacco-containing material and may, for example, include one or more of tobacco per se, different varieties of tobacco, tobacco derivatives, pelletized tobacco, extruded tobacco, expanded tobacco, reconstituted tobacco, ground tobacco, tobacco extract, homogenized tobacco or tobacco substitutes. In the case of tobacco, the solid material may be in the form of a rod of tobacco, a pod or plug of tobacco, loose tobacco, agglomerates, etc., and may be in relatively dry form or in relatively moist form for example. The tobacco may have been modified, for example chemically modified, for example had its pH modified so as to promote the release of selected constituents of the tobacco such as nicotine. Suitable solid materials may include other, non-tobacco, products, which, depending on the product, may or may not contain nicotine. The tobacco rod may be formed using a transparent material as a wrapping material, so that the user can see the tobacco. A particularly suitable material is NATUREFLEX, a biodegradable film made from renewable raw materials by Innovia Films Limited.

As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavorant may be impregnated in a porous solid material so as to impart flavor and/or other properties to that porous solid material. As such, the liquid or oil is a constituent of the solid material in which it is impregnated.

Although in the above examples the material was referred to as being a solid material or material in solid form, this need not necessarily be the case. In other examples, the material may be a fluid, for example a liquid.

The above embodiments are to be understood as illustrative examples of the invention. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. An apparatus for generating an inhalable medium, the apparatus comprising:
    a container for holding a liquid;
    an outer shell;
    an annular channel between the container and the outer shell;
    a heater for volatilizing liquid held in the container to generate a flow of at least one of a vapor or an aerosol in use; and
    an annular receptacle for receiving material;
    wherein the annular receptacle is located adjacent to and completely surrounds the heater such that in use, material received in the annular receptacle is heated by the heater, and wherein one or more constituents of material received in the annular receptacle in use are mixed with the flow of at least one of the vapor or the aerosol in use to produce the inhalable medium; and
    wherein the apparatus is arranged such that in use, the flow of at least one of the vapor or the aerosol passes radially out through the material received in the annular receptacle from the heater to the annular channel, thereby to entrain the one or more constituents of material in the flow of at least one of the vapor or the aerosol.

2. The apparatus according to claim 1, wherein the liquid container and the annular receptacle are an integral unit.

3. The apparatus according to claim 1, wherein the annular receptacle comprises two or more discrete receiving portions each for receiving a respective discrete portion of the material.

4. The apparatus according to claim 1, wherein the container is removable from the apparatus.

5. The apparatus according to claim 1, wherein the annular receptacle comprises one or more retainers for retaining material within the annular receptacle in use.

6. The apparatus according to claim 5, wherein the one or more retainers allow the at least one of the vapor or the aerosol to pass there-through, and prevent material received in the annular receptacle in use to pass there through.

7. The apparatus according to claim 1, wherein the annular receptacle has material received therein.

8. The apparatus according to claim 7, wherein the material is annular in shape.

9. The apparatus according to claim 7, wherein the material comprises a recess into which the heater is at least partially inserted.

10. The apparatus according to claim 7, wherein the material is contained in a self-supporting material container.

11. The apparatus according to claim 7, wherein the material is material in solid form.

12. The apparatus according to claim 11, wherein the solid material is or comprises a flavored material.

13. A method of generating an inhalable medium using an apparatus comprising a container for holding a liquid, an outer shell, an annular channel between the container and the outer shell, a heater for volatizing the liquid, and an annular receptacle for receiving material adjacent to and completely surrounding the heater, the method comprising:
    volatizing, using the heater, liquid held in the container to generate a flow of at least one of a vapor or an aerosol;
    heating, using the heater, material received in the annular receptacle; and
    passing the flow of at least one of the vapor or the aerosol radially out through the material received in the annular receptacle from the heater to the annular channel to mix one or more constituents of the material with the flow of at least one of the vapor or the aerosol by entraining the one or more constituents of the material in the flow of at least one of the vapor or the aerosol to produce the inhalable medium.

14. A cartridge for use with an apparatus for generating an inhalable medium, the cartridge comprising:
    a container for holding a liquid;
    an outer shell;
    an annular channel between the container and the outer shell;
    a heater for volatizing liquid held in the container to generate a flow of at least one of a vapor or an aerosol in use; and
    an annular receptacle for receiving material;
    wherein the annular receptacle is located adjacent to and completely surrounds the heater such that in use, material received in the annular receptacle is heated by the heater, and wherein one or more constituents of material received in the annular receptacle from the heater to the annular channel are mixed with the flow of at least one of the vapor or the aerosol in use to produce the inhalable medium; and
    wherein the cartridge is arranged such that in use, the flow of at least one of the vapor or the aerosol passes radially out through the material received in the annular receptacle, thereby to entrain the one or more constituents of the material in the flow of at least one of the vapor or the aerosol.

* * * * *